(12) United States Patent
Kuthi et al.

(10) Patent No.: US 7,901,930 B2
(45) Date of Patent: Mar. 8, 2011

(54) HIGH VOLTAGE NANOSECOND PULSE GENERATOR USING FAST RECOVERY DIODES FOR CELL ELECTRO-MANIPULATION

(75) Inventors: Andras Kuthi, Thousand Oaks, CA (US); Martin A. Gundersen, San Gabriel, CA (US)

(73) Assignee: University of Southern California, Los Angeles, CA (US)

( * ) Notice: Subject to any disclaimer, the term of this patent is extended or adjusted under 35 U.S.C. 154(b) by 0 days.

(21) Appl. No.: 12/703,002

(22) Filed: Feb. 9, 2010

(65) Prior Publication Data

US 2010/0141043 A1 Jun. 10, 2010

Related U.S. Application Data

(62) Division of application No. 11/279,697, filed on Apr. 13, 2006, now Pat. No. 7,767,433.

(60) Provisional application No. 60/673,949, filed on Apr. 22, 2005.

(51) Int. Cl.
*C12M 1/42* (2006.01)
*C12M 3/00* (2006.01)

(52) U.S. Cl. ............ 435/285.2; 435/173.6; 435/461

(58) Field of Classification Search ............ 435/173.6, 435/283.1, 285.2, 461; 327/304
See application file for complete search history.

(56) References Cited

U.S. PATENT DOCUMENTS

| | | |
|---|---|---|
| 3,624,416 A | 11/1971 | Bleickardt |
| 3,676,708 A | 7/1972 | Uchida |
| 3,699,361 A | 10/1972 | Bryden |
| 4,253,035 A | 2/1981 | Amitay |
| 4,442,362 A | 4/1984 | Rao |
| 4,758,736 A | 7/1988 | Agoston et al. |
| 6,008,038 A | 12/1999 | Kroger et al. |
| 6,483,362 B2 | 11/2002 | Otani et al. |
| 6,542,778 B1 | 4/2003 | Fuhr et al. |
| 2003/0170898 A1 | 9/2003 | Gundersen et al. |
| 2004/0254419 A1 | 12/2004 | Wang et al. |

OTHER PUBLICATIONS

Boff, A.N. et al. 1960. University Museum. Session IV: Applications of New Devices, 4.5 A New High-Speed Effect in Solid-State Diodes. Thursday, Feb. 11, 1960. Downloaded on May 7, 2009.

Grekhov, I.V. et al. 2000. Physical Basis for High-Power Semiconductor Nanosecond Opening Switches. IEEE Transactions on Plasma Science, vol. 28, 2000, pp. 1540-1544.

(Continued)

*Primary Examiner* — William H Beisner
*Assistant Examiner* — Michael Hobbs
(74) *Attorney, Agent, or Firm* — McDermott Will & Emery LLP

(57) ABSTRACT

A pulse generator circuit may include a diode configured to operate as an opening switch, a tank circuit in series with the diode having an admittance that is switchable from a first value to a second value that is different from the first value, and a switching system configured to cause the tank circuit to switch between the first value and the second value. The diode may saturate in less than 100 nanoseconds. A saturable core transformer may operate as a switch that controls the opening of the diode. The pulse generator may generate a plurality of pulses, each having a length of no more than 3 nanoseconds and an amplitude of at least 1 kilovolt. Electrodes may be connected to the pulse generator to deliver the plurality of pulses to biological cells.

7 Claims, 5 Drawing Sheets

OTHER PUBLICATIONS

Gundersen M.A. et al. 2004. Bipolar Nanosecond Pulse Generation Using Transmission Lines for Cell Electro-Manipulation. Power Modulator Symposium, 2004 and 2004 High-Voltage Workshop. Conference Record of the Twenty-Sixth International. IEEE, pp. 224-227.

Hewlett Packard. 1984. Application Note 918, Pulse and Waveform Generation with Step Recovery Diodes. Oct. 1984. 22 pages.

Hewlett Packard. 1968. Application Note 920, Harmonic Generation Using Step Recovery Diodes and SRD Modules. 34 pages.

Kotov Yu.A. et al. 1993. A Novel Nanosecond Semiconductor Opening Switch for Megavolt Repetitive Pulsed Power Technology: Experiment and Applications. In Proceedings of the 9th Int. IEEE Pulsed Power Conference, Albuquerque, NM, 1993, pp. 134-139.

Kuthi, A. et al. 2004. Bipolar Nanosecond Pulse Generation Using Transmission Lines for Cell Electro-Manipulation. Power Modulator Symposium, May 23-26, 2004 and 2004 High Voltage Workshop, Conference Record of the Twenty-Sixth International. IEEE, pp. 224-227.

Lyubutin S.K. et al. 1997. Repetitive Nanosecond All-Solid-State Pulsers Based on SOS Diodes. In IEEE 11th International Pulsed Power Conference, Baltimore, MD, pp. 992-998.

Moll, J.L. et al. 1969. Physical Modeling of the Step Recovery Diode for Pulse and Harmonic Generation Circuits. In Proceedings of the IEEE, vol. 57, No. 7, pp. 1250-1259.

Rukin S.N. 1999. High-Power Nanosecond Pulse Generators Based on Semiconductor Opening Switches (Review). Instruments and Experimental Techniques, vol. 42, No. 4, pp. 439-467.

Sun, Y. et al. 2006. Fluorescence Microscopy Imaging of Electropertubation in Mammalian Cells. Journal of Biomedical Optics, Mar./Apr. 2006, vol. 11, No. 2, section 1-1 to 1-8, UC Davis, Davis, California.

HIGH VOLTAGE NANOSECOND PULSE GENERATOR USING FAST RECOVERY DIODES FOR CELL ELECTRO-MANIPULATION

CROSS-REFERENCE TO RELATED APPLICATIONS

This application is a divisional application of U.S. patent application Ser. No. 11/279,697 now U.S. Pat. No. 7,767,433 B2, filed Apr. 13, 2006, entitled "High Voltage Nanosecond Pulse Generator Using Fast Recovery Diodes for Cell Electro-Manipulation," which is based upon and claims priority to U.S. Provisional Application Ser. No. 60/673,949, filed Apr. 22, 2005, entitled "Nanosecond Pulse Generator for Cell-Electro-Manipulation. " This application is also related to divisional U.S. patent application Ser. No. 12/409,707, entitled "High Voltage Nanosecond Pulse Generator Using Fast Recovery Diodes for Cell Electro-Manipulation". The entire content of all three applications is incorporated herein by reference.

STATEMENT REGARDING FEDERALLY SPONSORED RESEARCH

This invention was made with government support under the U.S. Air Force Office of Scientific Research Grant Nos. F29620-01-1-0387 and F49620-01-1-0495 and U.S. Army Research Office Grant No. DAAD 19-01-1-0698. The government has certain rights in the invention.

BACKGROUND

1. Field

This application relates to pulse generators and, more particularly, to pulse generators that may be used for electroperturbation of biological cells.

2. Description of Related Art

Ultra-short, high-field strength electronic pulses may be used in the electroperturbation of biological cells. The voltage induced across a cell membrane may depend on the pulse length and pulse amplitude. Pulses longer than ~1 μs may charge the outer cell membrane and lead to opening pores, either temporarily or permanently. Permanent openings may result in cell death. Pulses much shorter than ~1 μs can affect the cell interior without adversely affecting the outer cell membrane. Pulses lasting a few tens of nanoseconds and with a 2-10 MV/m amplitude may trigger apoptosis or programmed cell death.

Shorter and higher amplitude electronic pulses are useful for cell biology research to probe and manipulate intracellular structures such as nuclei and mitochondria.

Spark gap switched transmission lines have been used to generate ultra-short pulses. However, they may be physically large and have only a low repetition rate. They may also have only a relatively short lifetime, and provide erratic pulses with a large amount of jitter. The transmission line capacitance may also need to be charged rapidly in order to overvolt the spark gap to meet a fast rise time requirement.

Radio frequency MOSFET switched capacitors have also been used to generate ultra-short pulses. However, MOSFET switched capacitors may not be able to generate pulses that are narrower than 15-20 ns. This may be due to complications of MOSFET driving circuits and inherent limitations of many MOSFET devices.

SUMMARY

A pulse generator circuit may include a diode configured to operate as an opening switch, a tank circuit in series with the diode having an admittance that is switchable from a first value to a second value that is different from the first value, and a switching system configured to cause the tank circuit to switch between the first value and the second value.

The switching system may include a first and a second electronic switch. The first switch may be configured to cause the diode to be forward biased upon closure. The second switch may be configured to cause the diode to be reversed biased upon closure.

The diode may be configured to be forward biased and reverse biased at different times. The switching system may be configured to cause the admittance of the tank circuit to be at the first value while the diode is forward biased and to be at the second value while the diode is reverse biased.

The first value of the admittance may be approximately half of the second value.

The tank circuit may include a first and a second capacitance and a first and a second inductance. The product of the first capacitance and the first inductance may be approximately the same as the product of the second capacitance and the second inductance.

The switching system may be configured to include the first and the second capacitance and the first and the second inductance in the tank circuit while the diode is forward biased. The switching system may be configured to include the second capacitance and the second inductance in the tank circuit, but not the first capacitance and the first inductance, while the diode is reverse biased.

The switching system may be configured to transfer charge from the first capacitance to the second capacitance. The switching system may be configured to transfer charge only while the diode is forward biased.

A pulse generator circuit may include a diode that that is configured to operate as an opening switch and that saturates in less than 100 nanoseconds, and a saturable core transformer configured to operate as a switch that controls the opening of the diode.

The pulse generator may include a tank circuit that includes the saturable core transformer and that is in series with the diode The tank circuit may have an admittance that is switchable from a first value to a second value that is different from the first value.

The saturable core transformer may be configured to cause the admittance to switch from the first value to the second value. The first value of the admittance may be approximately half of the second value.

The tank circuit may include a first and a second capacitance.

The pulse generator may include a MOSFET configured to cause the first and the second capacitance to be part of the tank circuit while the diode is forward biased and to cause the second capacitance to be part of the tank circuit, but not the first capacitance, while the diode is reversed biased.

Apparatus for electropertubation of biological cells may include a pulse generator configured to generate a plurality of pulses, each having a length of no more than 3 nanoseconds and an amplitude of at least 1 kilovolt, and electrodes connected to the pulse generator configured to deliver the plurality of pulses to biological cells.

The pulse generator may be configured to deliver the plurality of pulses at a frequency of at least 100 kHz.

The pulse generator may include a diode that is configured to operate as an opening switch and that saturates in less than 100 nanoseconds.

These, as well as other components, steps, features, objects, benefits, and advantages, will now become clear from

DETAILED DESCRIPTION OF ILLUSTRATIVE EMBODIMENTS

Figure 1:
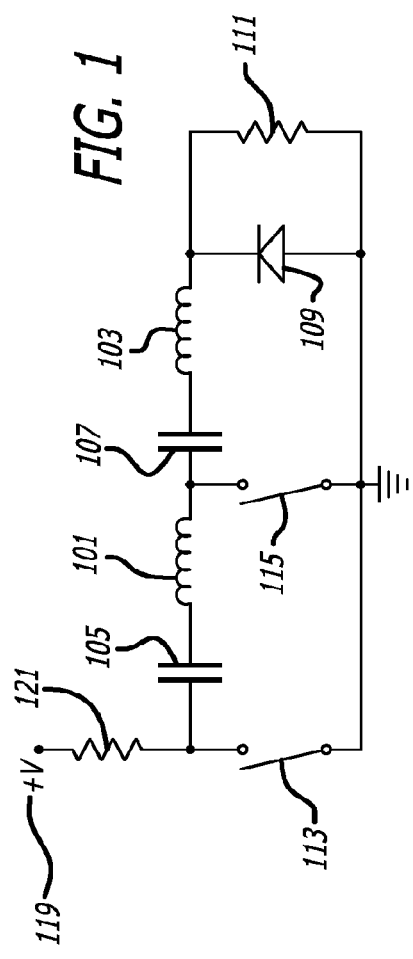
FIG. 1 is a simplified diode pulse generator.

FIG. 1 is a simplified diode pulse generator.

As shown in FIG. 1, the diode pulse generator may include a tank circuit consisting of inductances 101 and 103 and capacitances 105 and 107. The tank circuit may be connected in series with a diode 109 across which a load to be driven 111 may be connected. The pulse generator may include a switching system, such as switches 113 and 115, which may be electronic. A voltage supply 119 may be connected to the diode pulse generator through a resistance 121.

Before the beginning of a pulse cycle, the switch 113 may be open and the switch 115 may be closed. This may cause the capacitance 105 to fully charge and the capacitance 107 to fully discharge.

At the beginning of the pulse cycle, the switch 113 may be closed and the switch 115 may be opened. This may cause charge to transfer from the capacitance 105 to the capacitance 107. During this transfer, the current through the tank circuit may rise and fall in approximately a sinusoidal manner.

This current may cause the diode 109 to be forward-biased as it travels travel through it. During this process, charge may be stored in the depletion layer of the diode 109.

At the end of the half-cycle, switch 115 may be closed. During the next half-cycle, the current flow may reverse in direction, causing the diode 109 to be reverse-biased. During the first part of the second half-cycle, current may still flow through the diode 109 while charge in its depletion layer is being depleted. Once the charge is depleted, the current through the diode 109 stops, causing the diode to appear as an open switch. This may cause the current through the inductance 103 to commute from the diode 109 to the load 111. The diode 109 may thus be configured to act as a opening switch, interrupting the current in the inductance 103 and commuting it into the load 111.

Current may now travel through the load 111 until the energy stored in the tank circuit consisting of the capacitance 107 and the inductance 103 depletes, thus delivering a pulse into the load 111.

The component values in the diode pulse generator shown in FIG. 1 may be selected so as to cause the charge in the diode 109 to be depleted at approximately the peak of the reverse bias current during the second half of the pulse cycle. When this occurs, the current through the load 111 is at maximum at the moment the diode 109 switches open, thus maximizing the peak voltage across the load 111.

To effectuate this peak timing, the capacitances 105 and 107 may be substantially the same and the inductances 101 and 103 may be substantially the same. This assumes an ideal circuit with ideal switches and lossless circuit elements. In a real circuit, adjustments to these values may be made to compensate, as will be discussed detail below in connection with FIG. 2.

As may now be apparent, the composition of the tank circuit that is shown in FIG. 1 changes as a function of the status of the switch 115. When the switch 115 is open, the tank circuit consists of the capacitances 105 and 107 and the inductances 101 and 103. When the switch 115 is closed, the tank circuit consists of the capacitance 107 and the inductance 103, but not the capacitance 105 and the inductance 101.

When the capacitances 105 and 107 are approximately equal and the inductances 103 and 101 are approximately equal, the resonant frequency of both tank circuit configurations may be substantially the same. Resonant frequency is a function of the product of the inductance and the capacitance. When the switch 115 is open, the total inductance is twice the inductance of the inductance 101 or 103 (assuming that the inductance 101 is about equal to the inductance 103), but the total capacitance is one-half of the capacitance of the capacitance 105 or 107 (assuming that the capacitance 105 and the capacitance 107 are about equal). Thus, the L-C time constant is equal to the capacitance 107 times the inductance 103.

When the switch 115 is closed, the L-C time constant is again equal to the capacitance 107 times the inductance 103. Thus, the closing of the switch 115 may not materially alter the resonant frequency of the tank circuit when the capacitances 105 and 107 are the same and the inductances 101 and 103 are the same.

On the other hand, the admittance of the tank circuit does change with the status of the switch 115. Admittance is a function of the square root of the capacitance divided by the inductance. When the switch 115 goes from open to close, the capacitance doubles and the inductance halves. Thus, the admittance of the tank in the diode pulse generator shown in FIG. 1 doubles when the switch 115 is closed. In turn, this causes the depletion layer in the diode 109 to discharge in the reverse-biased mode twice as fast as it took to charge in the forward-biased mode. If the diode 109 is never allowed to saturate when the diode is forward-biased, this may result in the depletion layer of the diode 109 being discharged at the moment the current in the second half of the cycle peaks.

The maximum output voltage of the diode pulse generator illustrated in FIG. 1 may be substantially equal to the peak current after the diode 109 has switched open, multiplied by the load 111.

The presence of the load 111 on the diode pulse generator shown in FIG. 1 may cause the magnitude of the pulse to the load 111 to decay to zero.

The switch 113 may be opened at any time after the switch 115 closes to initiate the second part of the cycle. This may cause the capacitance 105 to again charge in preparation for the next pulse that may be generated.

After the pulse to the load 111 decays, the switch 115 may be opened to ready the diode pulse generator shown in FIG. 1 to deliver the next pulse. After the charges have stabilized, the next cycle leading to the next pulse may be initialized by closing the switch 115, followed by the actions described above in connection with the first cycle.

In order to create extremely narrow pulses, the switch 115 may need to open and close very quickly. One approach to providing this fast switching speed is to use a saturable core transformer to serve as the switch 115.

Figure 2:
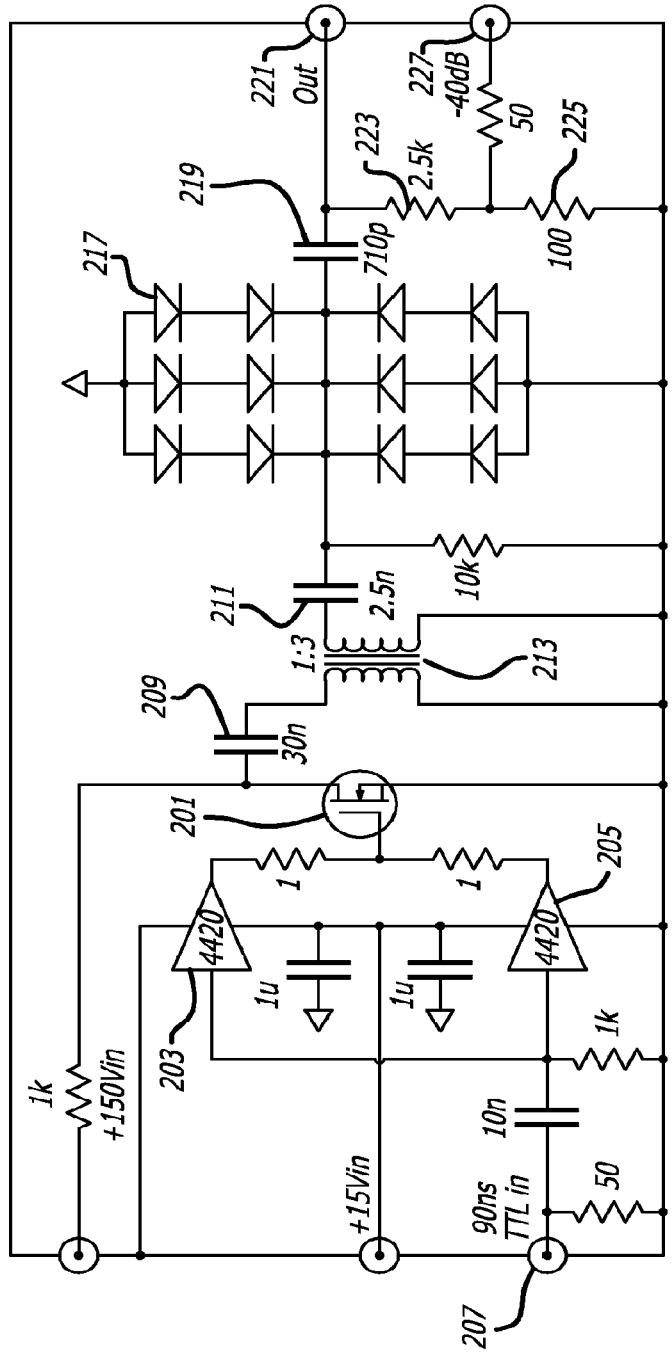
FIG. 2 is a diode pulse generator that utilizes a saturable core transformer.

FIG. 2 is a diode pulse generator that utilizes a saturable core transformer. The symbols and nomenclature that are shown in FIG. 2 are readily recognizable to the skilled artisan, thus obviating the need for a detailed description of every single component and connection. Instead, only selected areas of the circuit will be discussed.

As shown in FIG. 2, a MOSFET 201 may serve as the switch 113 shown in FIG. 1. This may be any type of MOSFET, such as an ATP 10035 JLL MOSFET.

The MOSFET 201 may be driven by a pair of drivers 203 and 205, such as an ON Semiconductor NCP4420, manufactured by Semiconductor Components Industries, LLC. The drivers may be triggered by the delivery of a pulse signal at an input 207. That input may be any type of signal, such as a 90 ns TTL pulse. This pulse may be repeated at a very high frequency.

A capacitance 209 in FIG. 2 may serve as the capacitance 105 in FIG. 1. Similarly, a capacitance 211 in FIG. 2 may serve as the capacitance 107 shown in FIG. 1. A saturable core transformer 213 may serve as the switch 115 shown in FIG. 1 and as the inductances 101 and 103 shown in FIG. 1. The capacitances 201 and 211 and the inherent inductances in the saturable core transformer 213 thus may serve as the tank circuit in FIG. 1.

In the absence of losses, the capacitance 209 may be substantially the same as the effective capacitance of the capacitance 211. The effective capacitance of the capacitance 211 my be its capacitance times the square of the ratio of turns in the saturable core transformer, which may be 1 to 3. Thus, the capacitance 211 may be equal to approximately nine times the capacitance 209 in a lossless system. In a practical system where there are losses, the value of the capacitance 209 may be larger to compensate, as reflected by the higher than nine-times value indicated in FIG. 2.

A diode array 217 may be used for the diode 109 shown in FIG. 1. The diode array 217 may consist of more than one diode in parallel and/or more than one diode in series. Connecting diodes in parallel may distribute the forward current across the diodes in the array, thus increasing the amount of time that current may be sent through the array before it becomes saturated. Connecting diodes in series may increase the amount of voltage that may be applied to the diodes when they are reverse-biased, thus allowing the output voltage of the pulse generator to be greater. The number of diodes that are placed in parallel and/or in series may be any number, so long as at least one diode is left. Using too may diodes may increase the capacitance of the circuit and slow its performance.

The diodes in the diode array 217 may be of any type, such as a MURS360, which is rated at 600 volts, 3 amps, and with a 75 ns reverse recovery time. One or more of the diodes may become saturated in less than 100 ns.

The saturable core transformer 213 may be configured to yield an energy storage inductance in its secondary winding that provides the needed fall time to achieve a desired output pulse width. The inductance current may decay as a function of the saturated secondary inductance of the transformer 213, divided by the load resistance that may be placed on an output 221. The minimum current that needs to be commuted into the load may be computed based on the desired peak output voltage, divided by the load resistance. The circuit may be designed to deliver an even higher output current to compensate for nonlinearities in the capacitance of the diode array 217, as well as other stray capacitances in the system.

The quarter period of the L-C circuit may be shorter than the diode recovery time to provide a fast current turn-off. A diode that is fully saturated with charge may delay its turn-off until after its recovery. As a consequence, the circuits shown in FIGS. 1 and 2 may be configured and operated such that the diodes do not saturate.

The fall time of the pulse that is delivered to the output 221 in the circuit shown in FIG. 2 may be shortened by the inclusion of a capacitance 219. A substantially attenuated version of the output may be generated by a resistor divider network, such as resistances 223 and 225, and delivered to an output test point 227.

The forward pumping current to the diode 109 may be equivalent to approximately $\pi$ times the square root of the inductance 103 multiplied by the capacitance 107. The capacitance 107 may be selected so that this forward pumping current lasts for approximately half of the recovery time of the diode 109.

The saturable core transformer 213 may be wound on an amorphous core from Toshiba, type SA 14×8×4.5. The external cord dimensions may be: OD=16.3 mm, ID=6.3 mm, H=7.5 mm, and the effective core area $A_{core}$=10.3 mm². The core may support a flux swing of $\phi$=10.94 µWb and may saturate at $B_{sat}$=0.55 T. The inductance factor for intermediate frequencies may be $A_L$=3 µH/turn².

The core frequency response may not extend to the range that is actually being used. In this instance, the specifications set forth above may only be approximate. The inductance may be strongly frequency and excitation dependent, and the switching characteristics may be slower than what is necessary for efficient operation. Because of these issues, the transformer may be matched to the circuit by trial and error. Operation with the shortest output pulse at the full voltage rating of the diodes may be achieved with a 1:3 turns ratio. The primary may be a single turn of 16 awg solid copper wire and the second may be three turns of 20 awg solid copper wire evenly distribute around a toroid.

The circuit shown in FIG. 2 may generate a pulse length of no more than 3 nanoseconds at an amplitude of 1 kV and at a frequency of at least 100 kHz.

Figure 3:
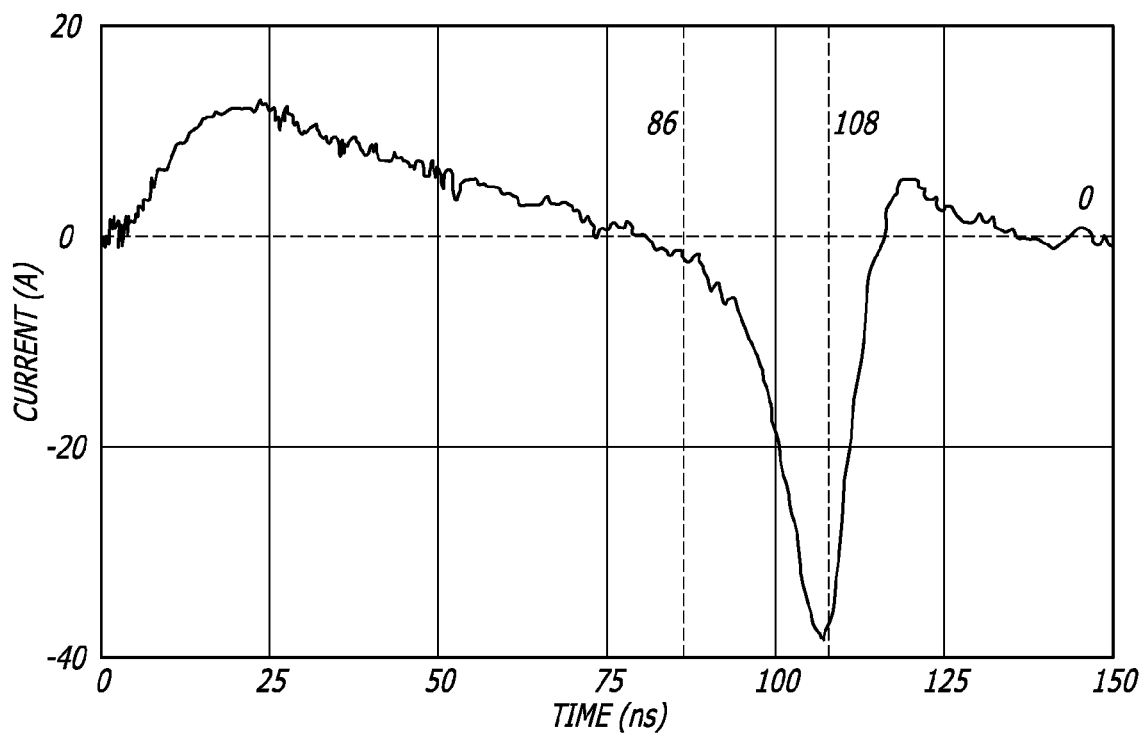
FIG. 3 illustrates current that may flow through the diode array 217 shown in FIG. 2.

FIG. 3 illustrates current that may flow through the diode array 217 shown in FIG. 2. As illustrated in FIG. 3, the diode array 217 may be forward-biased during approximately the first 86 ns. It may then be reverse-biased, following which the charge in its depletion layer may be quickly depleted and the diode switches off. This may open the circuit and commute the current from the diode array 217 to the load.

As can be seen from the values in FIG. 3, the saturated secondary inductance may be less than the designed value, and the peak current may be significantly higher. The higher current may compensate for the nonlinear diode capacitance and the losses of the saturable core. The forward diode pumping current may not be a pure half sine wave, as slow core saturation and resistive losses in the core and the primary MOSFET switch may cause distortion.

The circuits in FIGS. 1 and 2 may generate a unipolar pulse that is applied to a load. That unipolar pulse may instead or in addition first be converted into a bipolar pulse using any known approach.

One approach to convert the unipolar pulse into a bipolar pulse is to differentiate the unipolar pulse with a series capacitance. The resulting width of the pulse, however, may be more than is desired.

Figure 4:
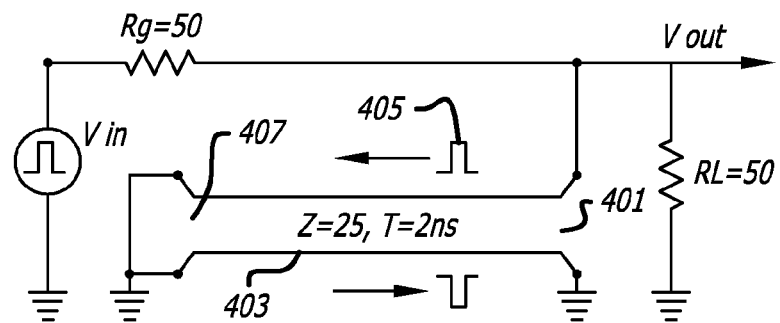
FIG. 4 illustrates a short transmission line used to convert a unipolar pulse to a bipolar pulse.

FIG. 4 illustrates a short transmission line used to convert a unipolar pulse to a bipolar pulse. As shown in FIG. 4, an input 401 to a short transmission line 403 may be connected to the unipolar pulse 405. The unipolar pulse 405 may travel to the end 407 of the transmission line 403 and be reflected back to the beginning 401 of the transmission line 403. The length of the transmission line 403 may be selected so as to cause the reflected pulse to arrive back at the input 401 just when the input pulse 405 falls. This length may be half the unipolar pulse width. The reflected pulse is inverted and is added to the input signal, resulting in a bipolar pulse.

The impedance of the transmission line 403 and the associated circuitry and connections may be selected so as to minimize spurious reflections, all in accordance with well known techniques. For example, the returning pulse may be terminated by the parallel combination of the pulse source and the load impedance. If these are both 50 ohms, the transmission line may be selected to have a 25 ohm impedance to match. Two 50 ohm coaxial cables may be connected in parallel to provide a transmission line with an effective impedance of 25 ohms.

Figure 5:
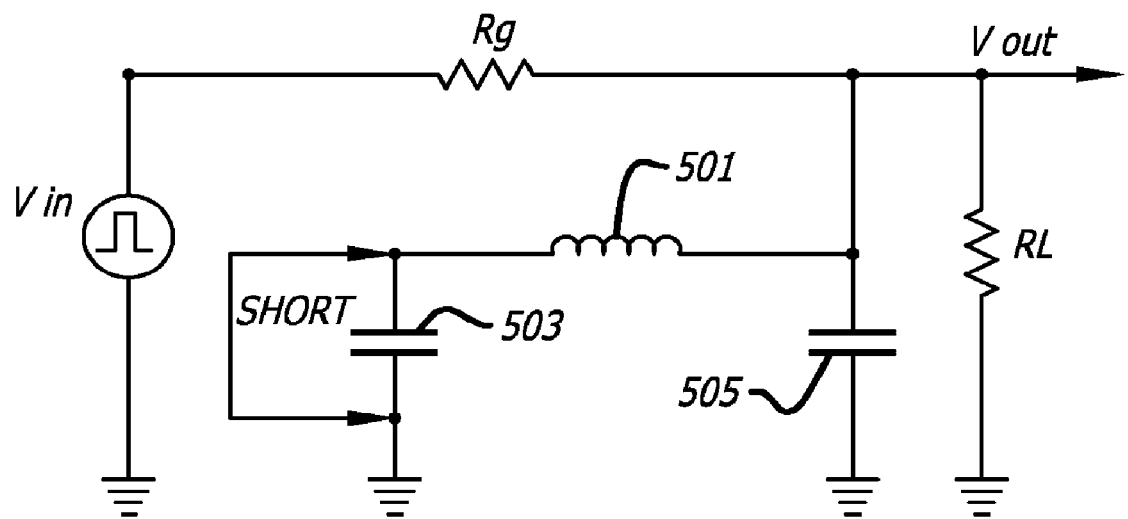
FIG. 5 illustrates a low-pass π network used to convert a unipolar pulse to a bipolar pulse.

FIG. 5 illustrates a low-pass π network used to convert a unipolar pulse to a bipolar pulse. The low-pass π network may be configured to provide electrical characteristics that are equivalent to the transmission line shown in FIG. 4. To a first order, for example, the inductance 501 may equal the delay time of the transmission line 403 multiplied by the impedance of the transmission line 403. Similarly, the total of the capacitances 503 and 505 may be calculated by dividing the delay time of the transmission line 403 in FIG. 4 by its impedance.

Figure 6A:
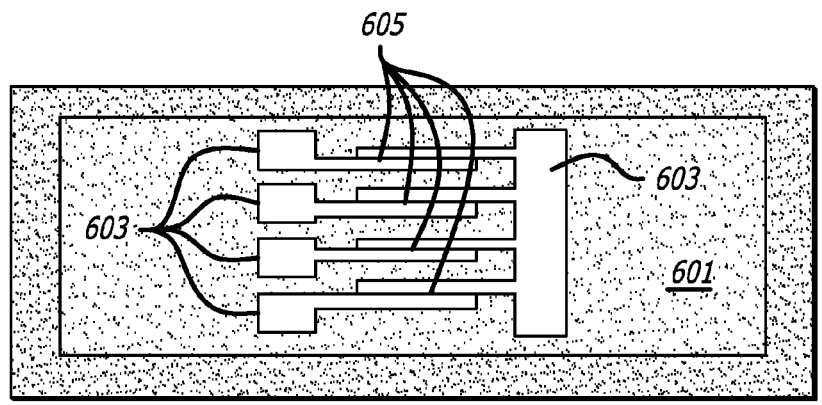
FIG. 6(a) illustrates an instrumented microscopic slide that may serve as a load for pulses generated by circuits, such as those shown in FIG. 1 and/or FIG. 2.

FIG. 6(a) illustrates an instrumented microscopic slide that may serve as a load for pulses generated by circuits, such as those shown in FIG. 1 and/or FIG. 2. As shown in FIG. 6(a), the slide may include a micro slide 601 on which several gold electrodes 603 may be deposited. The electrodes 603 may be positioned so as to form a plurality of channels 605 that may be of any width, such as approximately 100 μm.

Figure 6B:
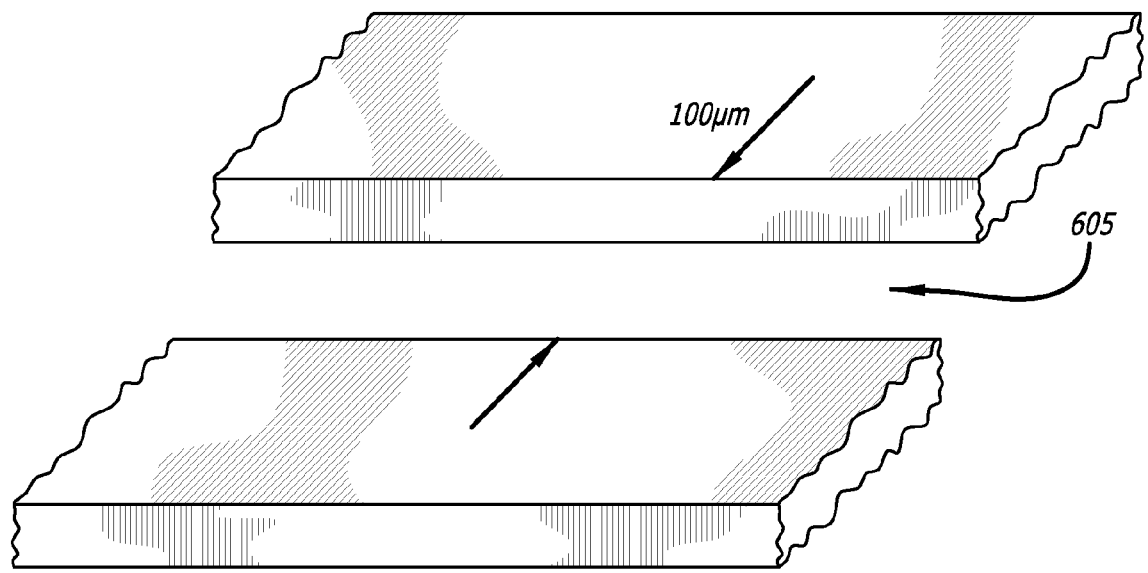
FIG. 6(b) illustrates an enlargement of one of the channels shown in FIG. 6(a).

FIG. 6(b) illustrates an enlargement of one of the channels 605 shown in FIG. 6(a).

A solution of cells may be placed within one or more of the channels 605. The micro slide 601 may be covered by another micro slide (not shown) and placed under a microscope (not shown) for study.

Figure 7:
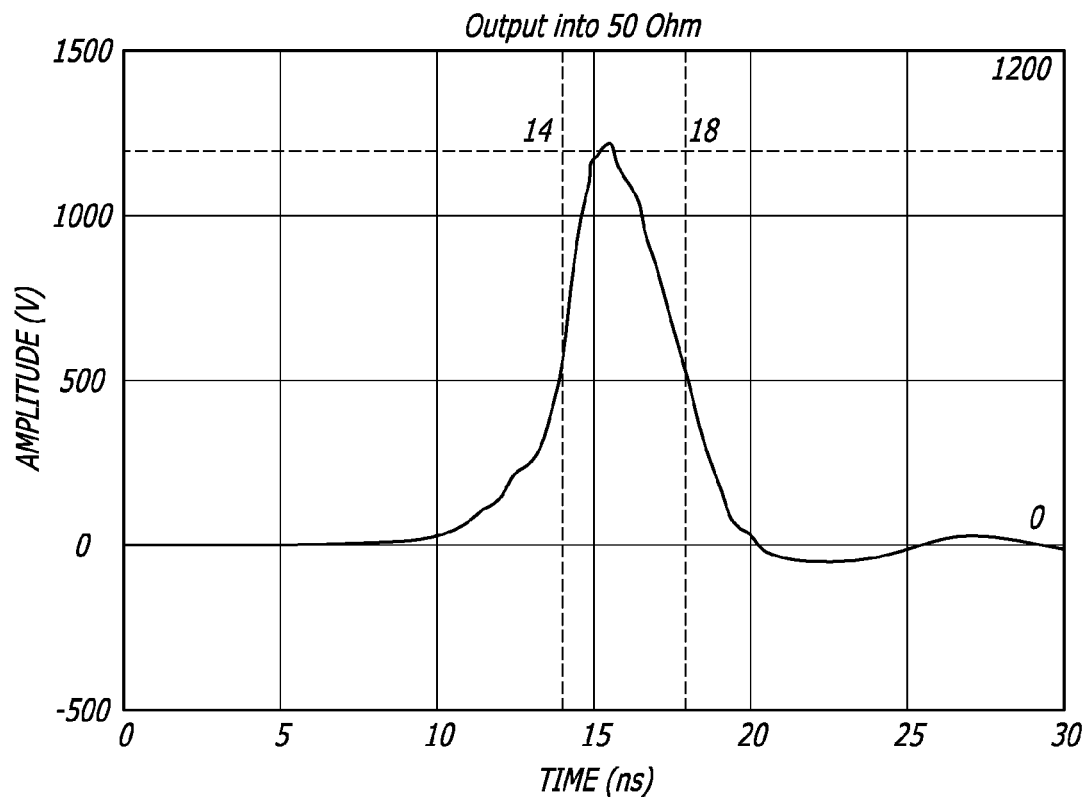
FIG. 7 illustrates a unipolar pulse that may be generated by the circuit shown in FIG. 2 when connected to a 50 ohm load.

FIG. 7 illustrates a unipolar pulse that may be generated by the circuit shown in FIG. 2 when connected to a 50 ohm load.

Figure 8:
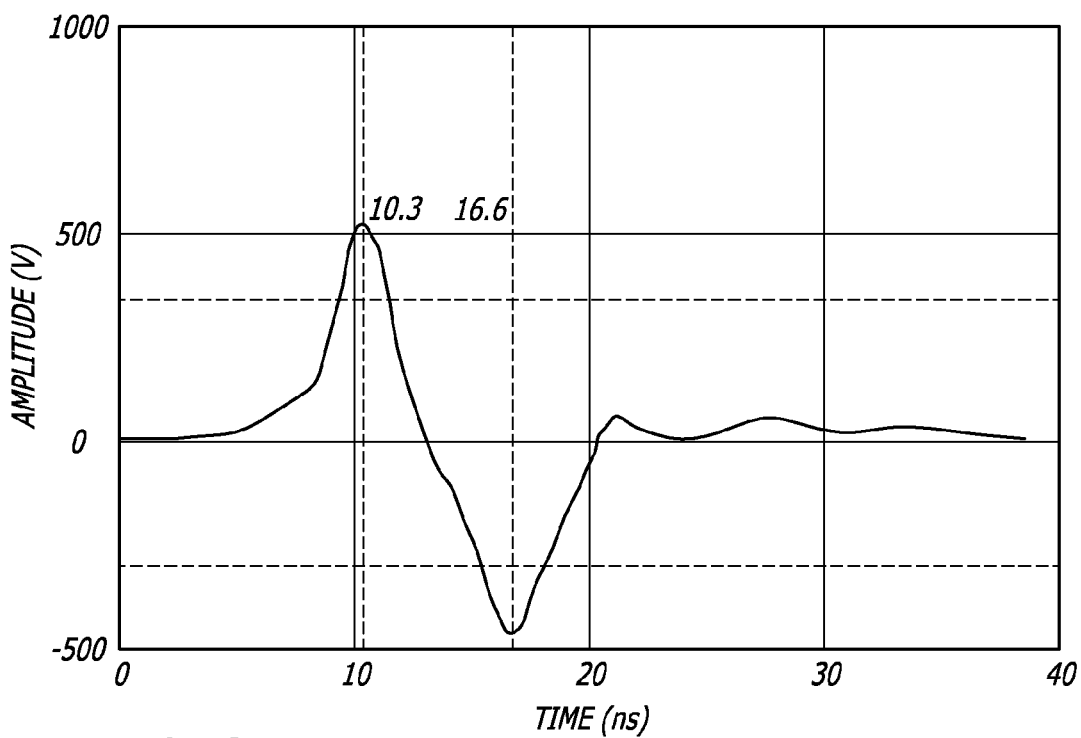
FIG. 8 illustrates a bipolar pulse that may be generated by the circuit shown in FIG. 2 when connected to a 50 ohm load.

FIG. 8 illustrates a bipolar pulse that may be generated by the circuit shown in FIG. 2 when connected to a 50 ohm load.

The components, steps, features, objects, benefits and advantages that have been discussed are merely illustrative. None of them, nor the discussions relating to them, are intended to limit the scope of protection in any way. Numerous other embodiments are also contemplated, including embodiments that have fewer, additional, and/or different components, steps, features, objects, benefits and advantages. The components and steps may also be arranged and ordered differently.

For example, although capacitances, inductances, resistances and switches have been illustrated in the drawings and/or discussed as single components, they may instead each be made of multiple components, cooperating together to perform the illustrated or recited function.

In short, the scope of protection is limited solely by the claims that now follow. That scope is intended to be as broad as is reasonably consistent with the language that is used in the claims and to encompass all structural and functional equivalents. Nothing that has been stated or illustrated is intended to cause a dedication of any component, step, feature, object, benefit, advantage, or equivalent to the public, regardless of whether it is recited in the claims.

The phrase "means for" when used in a claim embraces the corresponding structure and materials that have been described and their equivalents. Similarly, the phrase "step for" when used in a claim embraces the corresponding acts that have been described and their equivalents. The absence of these phrases means that the claim is not limited to any corresponding structures, materials, or acts.

We claim:

1. A pulse generator circuit comprising:
    a diode that that is configured to operate as an opening switch and that saturates in less than 100 nanoseconds; and
    a saturable core transformer configured to operate as a switch that controls the opening of the diode.

2. The pulse generator of claim 1 further comprising a tank circuit that includes the saturable core transformer and that is in series with the diode.

3. The pulse generator of claim 2 wherein the tank circuit has an admittance that is switchable from a first value to a second value that is different from the first value.

4. The pulse generator of claim 3 wherein the saturable core transformer is configured to cause the admittance to switch from the first value to the second value.

5. The pulse generator of claim 3 wherein the first value of the admittance is approximately half of the second value.

6. The pulse generator of claim 2 wherein the tank circuit include a first and a second capacitance.

7. The pulse generator of claim 6 wherein the diode is configured to be forward biased and reversed biased at different times and further comprising a MOSFET configured to cause the first and the second capacitance to be part of the tank circuit while the diode is forward biased and to cause the second capacitance to be part of the tank circuit, but not the first capacitance, while the diode is reversed biased.

* * * * *